(12) United States Patent
Nakashima et al.

(10) Patent No.: US 7,607,340 B2
(45) Date of Patent: Oct. 27, 2009

(54) GAS SENSOR

(75) Inventors: Takashi Nakashima, Aichi (JP); Yuichi Yamada, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 70 days.

(21) Appl. No.: 11/832,855

(22) Filed: Aug. 2, 2007

(65) Prior Publication Data

US 2008/0028831 A1 Feb. 7, 2008

(51) Int. Cl.
*G01N 9/00* (2006.01)

(52) U.S. Cl. .............. 73/31.05; 73/23.31; 73/21.32; 204/426; 204/428

(58) Field of Classification Search .............. 73/31.05; 204/426
See application file for complete search history.

(56) References Cited

U.S. PATENT DOCUMENTS

| | | | | |
|---|---|---|---|---|
| 4,507,192 A | * | 3/1985 | Ebizawa et al. | 204/428 |
| 6,327,891 B1 | * | 12/2001 | Noda et al. | 73/31.05 |
| 6,346,179 B1 | * | 2/2002 | Makino et al. | 204/428 |
| 6,401,521 B1 | * | 6/2002 | Nelson | 73/31.05 |
| 6,749,732 B2 | * | 6/2004 | Nakagawa et al. | 204/428 |
| 6,945,091 B2 | | 9/2005 | Nakagawa | |
| 7,045,047 B2 | | 5/2006 | Nakae et al. | |
| 7,159,447 B2 | * | 1/2007 | Nakagawa | 73/31.05 |
| 2002/0053233 A1 | | 5/2002 | Grieser et al. | |
| 2003/0121782 A1 | * | 7/2003 | Atsumi et al. | 204/424 |
| 2005/0241937 A1 | * | 11/2005 | Shichida et al. | 204/424 |

* cited by examiner

*Primary Examiner*—Hezron Williams
*Assistant Examiner*—Rachel Black
(74) *Attorney, Agent, or Firm*—Sughrue Mion, PLLC

(57) ABSTRACT

In a protector (100) for protecting a detecting portion (11) of a sensor element (10) of a gas sensor (1), the opening area of individual inner introduction holes (130) and (140) formed in an inner protector (120) is 3.5 mm² or less. In this manner, the amount and size of water droplets able to pass through the inner introduction holes (130) and (140) and to adhere to the sensor element (10) is restricted. In order to ensure good gas replaceability between the interior and the exterior of the inner protector (120) so as to attain quick gas response, the total opening area of the inner introduction holes (130) and (140) is 10 mm² or more.

12 Claims, 9 Drawing Sheets

GAS SENSOR

BACKGROUND OF THE INVENTION

1. Field of the Invention

The present invention relates to a gas sensor having a protector for preventing water droplets present in exhaust from adhering to a detecting element exposed to exhaust gas.

2. Description of the Related Art

Conventionally, a gas sensor is known having a detecting element which generates an electromotive force having a magnitude corresponding to the concentration of a specific gas; for example, NOx (nitrogen oxides) or oxygen, contained in exhaust gas of an automobile or the like or whose resistance varies with concentration. The gas sensor is attached, for use, to an exhaust pipe of an automobile or the like. Since the detecting element is exposed to exhaust gas of high temperature, subjecting the detecting element to thermal shock caused by adhering water droplets contained in exhaust gas may crack or break the detecting element. In order to cope with this problem, the gas sensor is provided with a protector for covering the detecting element, thereby protecting the detecting element from adhering water droplets (refer to, for example, Patent Document 1).

The protector of the gas sensor of Patent Document 1 has a dual structure consisting of an outer tubular member and an inner tubular member. A front end portion (a lower portion when the gas sensor is attached) of the outer tubular member has introduction holes for introducing exhaust gas toward a clearance between the outer tubular member and the inner tubular member (hereinafter, also referred to as a "gas separation chamber"). Guide portions are provided at respective introduction holes of the outer tubular member for causing exhaust gas introduced into the gas separation chamber to swirl around the outer circumferential surface of a side wall of the inner tubular member. Inertial force associated with the swirl separates a gas component and water, which is heavy relative to the gas component, from one another. A rear end portion (an upper portion when the gas sensor is attached) of the inner tubular member has introduction holes for introducing the gas component, which is separated in the gas separation chamber, into the interior of the inner tubular member.

[Patent Document 1] Japanese Patent Application Laid-Open (kokai) No. 2004-125702

3. Problems to be Solved by the Invention

However, even when a gas component and water are separated from one another as in the case of Patent Document 1, water, together with the gas component, may enter the interior of the inner tubular member. This depends on the velocity of exhaust gas introduced into the interior of the outer tubular member, the mass of the water droplet, the position of the gas sensor attached to an exhaust pipe, and other factors. Adhesion of a large water droplet to the detecting element may impart thermal shock to the detecting element to a degree so as to crack or break the detecting element.

SUMMARY OF THE INVENTION

The present invention has been achieved in order to solve the above-noted problems, and an object thereof is to provide a gas sensor having a protector which can effectively prevent water droplets present in exhaust gas from adhering to a detecting element exposed to the exhaust gas while also maintaining good gas replaceability.

The above object has been achieved by providing, in a first aspect of the invention (1), a gas sensor comprising a detecting element having detecting portion provided at a front end portion of the detecting element and adapted to detect a specific gas component contained in a gas-to-be-measured; a housing radially enclosing the detecting element, the detecting portion of the detecting element projecting from a front end of the housing; an inner protector having a rear end portion fixed to a front end portion of the housing and accommodating the detecting portion of the detecting element inside the inner protector, said inner protector having a plurality of inner introduction holes for introducing the gas-to-be-measured into the interior of the inner protector, the inner introduction holes being formed in a circumferential wall of the inner protector along a circumferential direction and being located rearward of a front end of the detecting element; and a cylindrical outer protector radially enclosing the inner protector such that a clearance is present between the inner protector and the outer protector, the outer protector having a rear end portion fixed to the front end portion of the housing and a plurality of outer introduction holes for introducing the gas-to-be-measured into the clearance, and the outer introduction holes being formed in a circumferential wall of the outer protector along a circumferential direction and located frontward of the inner introduction holes of the inner protector with respect to an axial direction of the gas sensor. In the gas sensor, the inner introduction holes individually have an opening area of 3.5 mm$^2$ or less, and the total opening area of the inner introduction holes is 10 mm$^2$ or more.

In a gas sensor of the invention according to a second aspect (2), in addition to the configuration of the invention according to (1) above, the inner introduction holes individually have an opening area of 2 mm$^2$ or less.

In a gas sensor of the invention according to a third aspect (3), in addition to the configuration of the invention according to (1) or (2) above, the inner introduction holes individually have a minimum opening length of 2 mm or less.

In a gas sensor of the invention according to a fourth aspect (4), in addition to the configuration of the invention according to any one of (1) to (3) above, the inner protector has six or more inner introduction holes.

In a gas sensor of the invention according to a fifth aspect (5), in addition to the configuration of the invention according to any one of (1) to (4) above, the inner protector has eight or more inner introduction holes.

In a gas sensor of the invention according to a sixth aspect (6), in addition to the configuration of the invention according to any one of (1) to (5) above, the circumferential wall of the inner protector has a taper portion whose diameter radially reduces toward a front end of the inner protector, and the inner introduction holes are formed in the taper portion.

In a gas sensor of the invention according to a seventh aspect (7), in addition to the configuration of the invention according to (6) above, the inner protector has a tubular portion continuous with a front end of the taper portion; the detecting element has a gas introduction portion for introducing the gas-to-be-measured into the interior of the detecting portion; and the gas introduction portion is disposed such that the gas introduction portion faces, in a crossing manner, a boundary between the taper portion and the tubular portion.

In a gas sensor of an invention according to an eighth aspect (8), in addition to the configuration of the invention according to any one of (1) to (7) above, the inner introduction holes are divided into a plurality of first inner introduction holes arranged circumferentially at a first position with respect to the axial direction and a plurality of second inner introduction holes arranged circumferentially at a second position located rearward of the first position with respect to the axial direction.

In a gas sensor of the invention according to a ninth aspect (9), in addition to the configuration of the invention according to (8) above, the plurality of the first inner introduction holes and the plurality of the second inner introduction holes are arranged so as not to overlap one another in a circumferential direction.

In a gas sensor of the invention according to a tenth aspect (10), in addition to the configuration of the invention according to (8) or (9) above, the detecting element has a gas introduction portion for introducing the gas-to-be-measured into the interior of the detecting portion, and the gas introduction portion is disposed between the first inner introduction holes and the second inner introduction holes with respect to the axial direction.

In a gas sensor of the invention according to an eleventh aspect (11), in addition to the configuration of the invention according to (10) above, the number of the first inner introduction holes is smaller than the number of the second inner introduction holes.

Effect of the Invention:

In the gas sensor of the invention according to (1) above, the inner introduction holes provided in the inner protector and located rearward of the front end of the detecting element individually have an opening area of 3.5 $mm^2$ or less, thereby preventing entry of a water droplet having a diameter greater than the size of the opening of the inner introduction hole inside the inner protector through the inner introduction holes. This restricts the amount and size of water droplets which could adhere to the detecting portion of the detecting element accommodated within the inner protector. Thus, the amount of adhering water droplets, if any, can be very small, so that the energy of thermal shock imparted to the detecting element becomes small, to thereby prevent cracking, breakage, or the like. The total opening area of all the inner introduction holes provided in the inner protector is 10 $mm^2$ or more. Therefore, even though an individual inner introduction hole has a small opening area of 3.5 $mm^2$ or less, the entire inner protector has a sufficiently large opening area of inner introduction holes. Therefore, gas replaceability does not suffer, so that the detecting element can exhibit sufficiently fast gas response.

Limiting the opening area of the individual inner introduction holes to 2 $mm^2$ or less restricts, to a greater extent, the amount and size of water droplets which could adhere to the detecting portion of the detecting element accommodated within the inner protector, so that cracking, breakage, or the like can effectively be prevented to a greater extent.

The opening area of an individual inner introduction hole is the area of an opening corresponding to an inner introduction hole as viewed when the inner protector is projected on a predetermined plane. The total opening area of the inner introduction holes is the total area of openings of all the inner introduction holes as viewed when the inner protector is projected on a predetermined plane. No particular limitation is imposed on the outer introduction holes of the outer protector, so long as the outer introduction holes are located frontward of the position of the inner introduction holes of the inner protector. Specifically, the front ends of the outer introduction holes may be located frontward of the front ends of the inner introduction holes. Preferably, in order to effectively protect the detecting element from adhering water droplets, the rear ends of the outer introduction holes are located frontward of the front ends of the inner introduction holes. Furthermore, preferably, the outer introduction holes and the inner introduction holes are respectively formed at circumferentially equal intervals so as to eliminate the need to consider orientation, position, etc., of the gas sensor when the gas sensor is attached to an exhaust pipe.

Furthermore, preferably, the minimum opening length of the individual inner introduction holes is 2 mm or less. As mentioned above, the smaller the opening area of an individual inner introduction hole, the greater its effectiveness in preventing cracking of the detecting element. Limiting the minimum opening length of an individual inner introduction hole to 2 mm or less prevents passage of a spherical water droplet having a diameter greater than 2 mm through the inner introduction holes. This more effectively restricts the amount and size of water droplets which could adhere to the detecting portion of the detecting element accommodated within the inner protector, so that cracking, breakage, or the like can be prevented.

Notably, "the minimum opening length of the individual inner introduction holes" is the length of a shortest line segment passing through the center (center of gravity) of the inner introduction hole. For example, in the case of an elliptic shape, it is the length of a shortest line segment passing through the center of gravity of the ellipse. In the case of a circular shape, it is the diameter of the circle.

Preferably, the inner protector has six or more inner introduction holes. This allows a further reduction in the opening area of the individual inner introduction holes while the total opening area of all the inner introduction holes is maintained at 10 $mm^2$ or more. Thus, cracking, breakage, etc., of the detecting element accommodated within the inner protector can effectively be prevented to a greater extent. More preferably, eight or more inner introduction holes are formed.

The inner protector may assume a cylindrical shape or may be such that the circumferential wall of the inner protector has, in its intermediate region, a taper portion whose diameter radially reduces toward a front end of the inner protector. In the case where the inner protector has a taper portion, preferably, the inner introduction holes are formed in the taper portion. Even when a water droplet smaller than the inner introduction hole enters the inner protector, the water droplet adheres to a portion of the detecting element which is located rearward of the detecting portion of the detecting element and which has a relatively low temperature. Thus, it is unlikely that the detecting portion of the detecting element becomes subjected to thermal shock, so that cracking, breakage, or the like can be prevented to a greater extent.

In the case where the inner introduction holes are formed in the taper portion, preferably, the gas introduction portion of the detecting element is disposed such that the gas introduction portion faces, in a crossing manner, the boundary between the taper portion and the tubular portion continuous with the front end of the taper portion. The gas introduction portion is adapted to introduce the gas-to-be-measured into the interior of the detecting portion of the detecting element. By forming the gas introduction portion such that the gas introduction portion faces both the taper portion and the tubular portion, the distance between the inner introduction holes and the gas introduction portion is shortened, whereby the gas-to-be-measured can be promptly introduced to the detecting portion. As a result, while cracking, breakage, or the like of the detecting element is more effectively prevented, the gas response of the detecting element can be quickened.

In manufacture of the inner protector which enhances the protection of the detecting element against adhering water droplets and which exhibits sufficient gas replaceability (gas replacement rate), the greater the reduction in the opening area of the inner introduction hole, the greater the required increase in the number of inner introduction holes. However, merely increasing the number of inner introduction holes results in a close arrangement of the inner introduction holes. That is, the inner introduction holes are circumferentially arranged in the form of perforations, possibly resulting in a failure to maintain strength of the inner protector. In order to cope with this problem, by dividing the inner introduction holes into those arranged circumferentially at the first position with respect to the axial direction and those arranged circumferentially at the second position with respect to the axial direction according to the eighth (8) aspect of the invention, the distance between a certain inner introduction hole and another inner introduction hole located closest to the former inner introduction hole can be increased, whereby the strength of the inner protector can be enhanced.

In the case where the first position is located closer to the front end of the inner protector, preferably, the outer introduction holes are located frontward of the first inner introduction holes of the inner protector. This includes a mode in which the outer introduction holes and the inner introduction holes overlap one another such that the front ends of the outer introduction holes are located frontward of the front ends of the first inner introduction holes. However, in order to effectively protect the detecting element from adhering water droplets, more preferably, the rear ends of the outer introduction holes are located frontward of the front ends of the first inner introduction holes. The first inner introduction holes formed at the first position and the second inner introduction holes formed at the second position may entirely or partially overlap one another with respect to the axial direction or may not overlap one another with respect to the axial direction.

Furthermore, preferably, according to the ninth (9) aspect of the invention, the first inner introduction holes arranged circumferentially at the first position with respect to the axial direction do not overlap in the circumferential direction with the second inner introduction holes arranged circumferentially at the second position with respect to the axial direction. This enables an increase in the distance between a certain inner introduction hole and another inner introduction hole located closest, with respect to the axial direction, to the former inner introduction hole. Thus, the strength of the inner protector can be enhanced more reliably.

Preferably, according to a tenth (10) aspect of the invention, the detecting element has a gas introduction portion for introducing the gas-to-be-measured into the interior of the detecting portion, and the gas introduction portion is disposed between the first inner introduction holes and the second inner introduction holes with respect to the axial direction. The gas introduction portion is adapted to expose the gas-to-be-measured to the detecting portion of the detecting element. By disposing the gas introduction portion between the first inner introduction holes and the second inner introduction holes with respect to the axial direction, the distances between the first inner introduction holes and the gas introduction portion and between the second inner introduction holes and the gas introduction portion are shortened, whereby the gas-to-be-measured can promptly be delivered to the detecting portion. Thus, the gas response of the detecting element can be quickened.

Furthermore, preferably, the number of the first introduction holes is smaller than the number of the second introduction holes. More specifically, preferably, the number of the second inner introduction holes disposed rearward of the gas introduction portion is greater than the number of the first inner introduction holes disposed frontward of the gas introduction portion. The gas-to-be-measured which is introduced into the inner protector through the inner introduction holes flows toward the front end of the inner protector. Therefore, by providing the second inner introduction holes disposed rearward of the gas introduction portion in a greater number, the gas-to-be-measured introduced into the inner protector can be exposed to the gas introduction portion in a greater amount. Thus, the gas response of the detecting element can be enhanced.

DESCRIPTION OF REFERENCE NUMERALS

Figure 1:
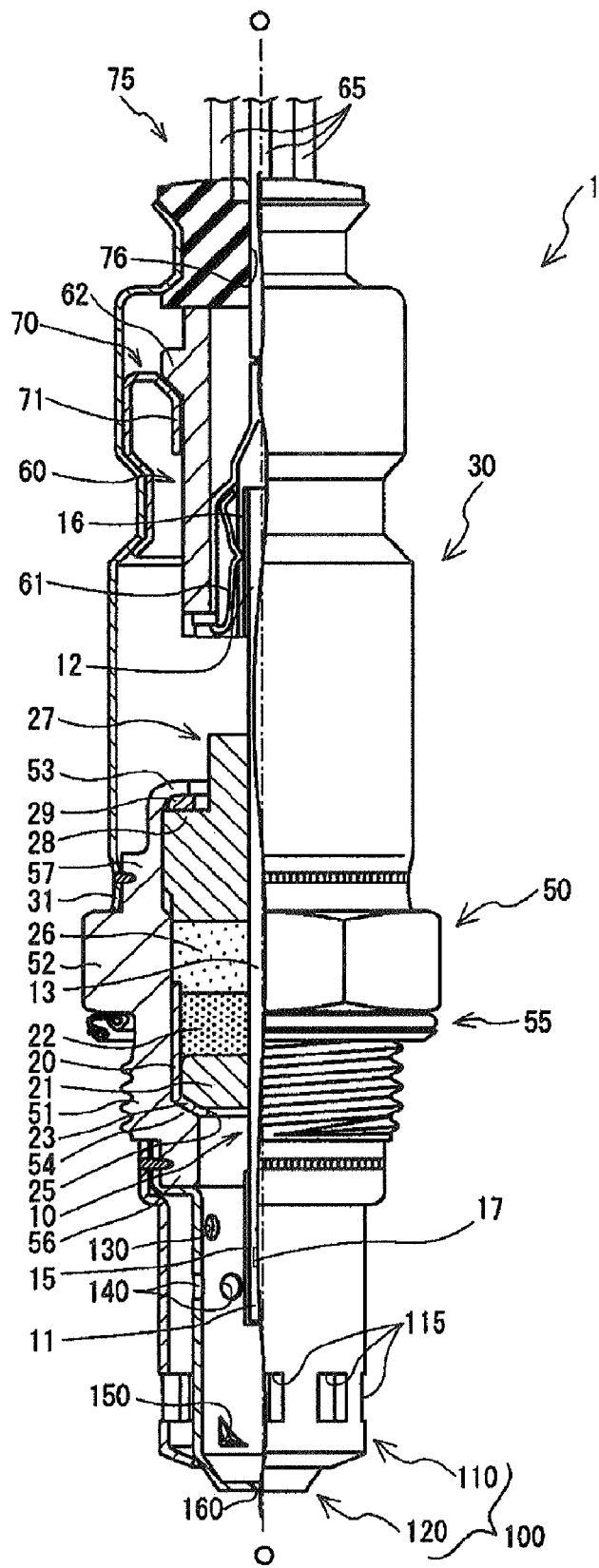
FIG. 1 is a partial sectional view of a gas sensor 1 according to a first embodiment of the present invention.

Reference numerals used to identify various structural features in the drawings include the following.
1, 500 gas sensor
10, 510 sensor element
11, 511 detecting portion
17, 517 gas introduction portion
50, 550 metallic shell
56 front-end engaging-portion
110, 610 outer protector
115, 615 outer introduction hole
119, 619 gas separation chamber
120, 620 inner protector
121, 621 rear end portion
130, 140, 630 inner introduction hole

DETAILED DESCRIPTION OF THE PREFERRED EMBODIMENTS

A gas sensor according to a first embodiment of the present invention will next be described with reference to the drawings. However, the present invention should not be construed as being limited thereto.

Figure 2:
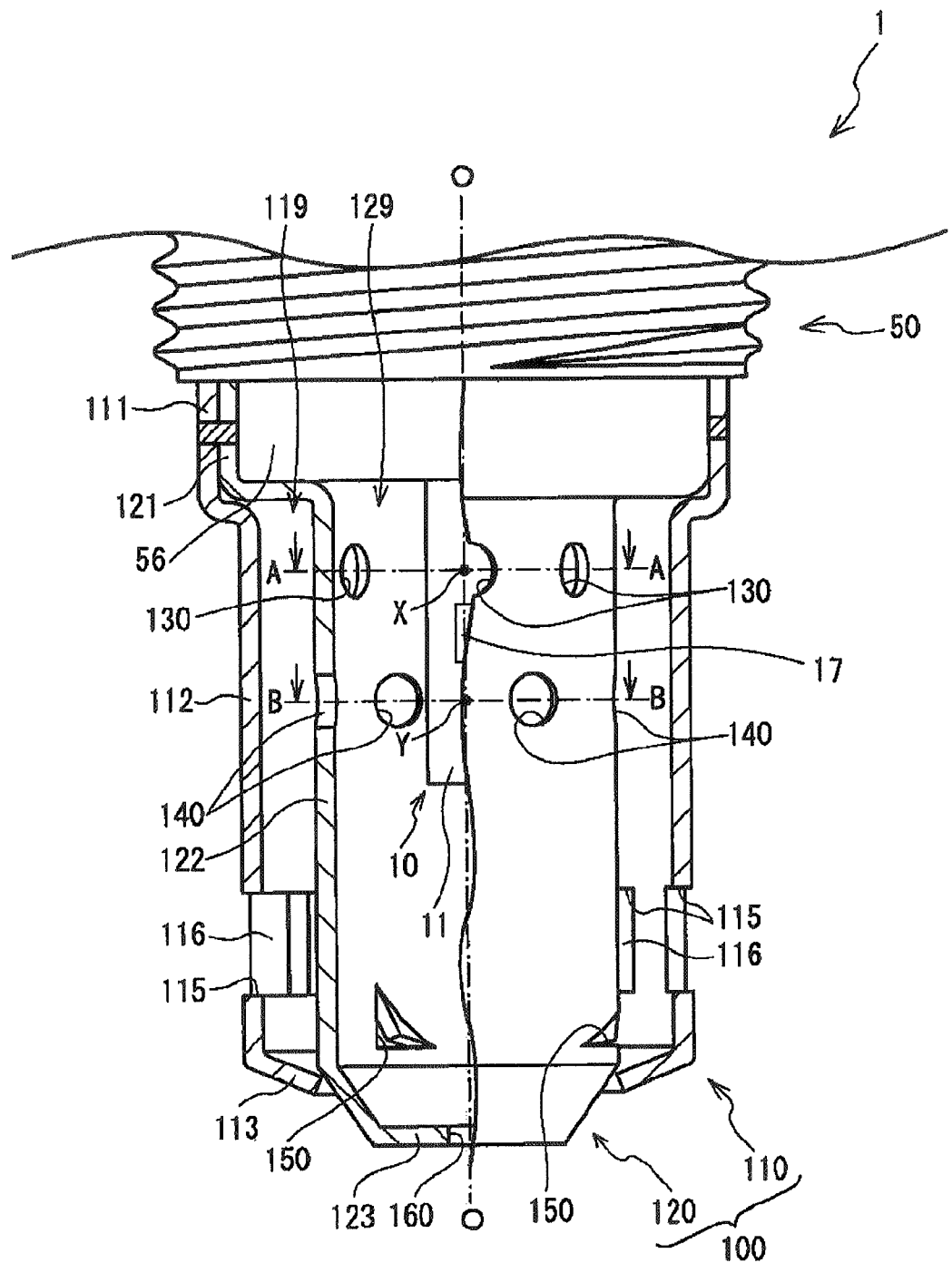
FIG. 2 is a partial sectional view on an enlarged scale of a front end portion of the gas sensor 1 according to the first embodiment.

First, the structure of a gas sensor 1 will be described, by way of example, with reference to FIGS. 1 and 2. FIG. 1 is a partial sectional view of the gas sensor 1. FIG. 2 is a partial sectional view on an enlarged scale of a front end portion of the gas sensor 1. Notably, in FIGS. 1 and 2, the direction of an axis O (represented by a dash-dot line) of the gas sensor 1 coincides with the vertical direction. In the following description, a side toward a detecting portion 11 of a sensor element 10 held in the interior of the gas sensor 1 is referred to as a front-end side of the gas sensor 1, and a side toward a rear end portion 12 is referred to as a rear-end side of the gas sensor 1.

The gas sensor 1 shown in FIG. 1 is attached to an exhaust pipe of an automobile (not shown). The detecting portion 11 of the sensor element 10 held in the interior of the gas sensor 1 is exposed to exhaust gas which flows through the exhaust pipe, for detecting the air/fuel ratio of the exhaust gas from the oxygen concentration of the exhaust gas; i.e., the gas sensor 1 is a so-called full-range air/fuel ratio sensor.

In a configuration well known to those skilled in the art, the sensor element 10 assumes the form of a strip extending in the direction of the axis O and is a generally rectangular columnar laminate comprising a gas-detecting element for detecting oxygen concentration and a heater element for quickly activating the gas-detecting element. The gas-detecting element is composed of a solid electrolyte body (not shown) which predominantly contains zirconia, and detecting electrodes (not shown) which predominantly contain platinum. The detecting electrodes are disposed at the detecting portion 11 located at the front end of the sensor element 10. Also, the sensor element 10 has a gas introduction portion 17 for introducing exhaust gas into the interior of the detecting portion 11. In order to protect the detecting electrodes from poisoning by exhaust gas, the detecting portion 11 of the sensor element 10 is covered with a protection layer 15. The rear end portion 12 of the sensor element 10 has five electrode pads 16 (one of which is shown in FIG. 1) for allowing external connection with electrodes extending from the gas-detecting element and from the heater element. Notably, in the description of the present embodiment, the sensor element 10 corresponds to the "detecting element.". However, strictly speaking, the detecting element does not necessarily include the heater element; thus, the gas-detecting element corresponds to the "detecting element" of the claims appended hereto.

A closed-bottomed tubular metal cup 20 is disposed slightly frontward of the axial center of a trunk portion 13 of the sensor element 10 in such manner that the sensor element 10 is inserted through the interior of the metal cup 20 with the detecting portion 11 projecting from an opening 25 formed in a bottom of the metal cup 20. The metal cup 20 is a member for holding the sensor element 10 in a metallic shell 50. A front-end peripheral-portion 23 located at a peripheral portion of the bottom of the metal cup 20 is tapered toward a tubular wall portion of the metal cup 20. The metal cup 20 contains a ceramic ring 21 made of alumina and a talc ring 22 formed by compacting a talc powder, so that the sensor element 10 is inserted through the ceramic ring 21 and through the talc ring 22. The talc ring 22 is crushed within the metal cup 20 so as to tightly fill an associated space, thereby holding the sensor element 10 in position in the metal cup 20.

An assembly of the metal cup 20 and the sensor element 10 is circumferentially enclosed by and held the tubular metallic shell 50. The metallic shell 50 is adapted to fixedly attach the gas sensor 1 to an exhaust pipe of an automobile (not shown). The metallic shell 50 is formed from a low-carbon steel such as SUS430 and has an externally threaded portion 51 which is formed on an outer circumferential surface of the metallic shell 50 and located on a side toward the front end of the metallic shell 50. The metallic shell 50 has a front-end engaging-portion 56 which is located frontward of the externally threaded portion 51 and engaged with a protector 100, described below. The metallic shell 50 also has a tool engagement portion 52 formed at an axially central portion of an outer circumferential surface of the metallic shell 50 for engaging a mounting tool. In order to prevent leakage of gas when the gas sensor 1 is attached to the exhaust pipe, a gasket 55 is fitted to a portion of the metallic shell 50 between the front end face of the tool engagement portion 52 and the rear end of the externally threaded portion 51. The metallic shell 50 further has a rear-end engaging-portion 57 located rearward of the tool engagement portion 52 and with which a sheath 30 described below is engaged, and a crimp portion 53 located rearward of the rear-end engaging-portion 57 and adapted to crimp-hold the sensor element 10 in the metallic shell 50. Notably, the metallic shell 50 corresponds to the "housing" in the claims appended hereto.

The metallic shell 50 has a stepped portion 54 on its inner circumferential surface at a position substantially corresponding to the externally threaded portion 51. The front-end peripheral-portion 23 of the metal cup 20 which holds the sensor element 10 engages with the stepped portion 54. Furthermore, a talc ring 26 is placed in the metallic shell 50 along the inner circumference of the metallic shell 50 from the rear side of the metal cup 20 so that the sensor element 10 is inserted through the talc ring 26. A tubular sleeve 27 is fitted into the metallic shell 50 so as to press the talc ring 26 from the rear side of the talc ring 26. The sleeve 27 has a step-like shoulder portion 28 formed on the outer circumferential surface of a rear end portion of the sleeve 27. An annular crimp packing 29 is disposed on the shoulder portion 28. In this condition, the crimp portion 53 of the metallic shell 50 is crimped so as to press the shoulder portion 28 of the sleeve 27 frontward via the crimp packing 29. Being pressed by the sleeve 27, the talc ring 26 is crushed within the metallic shell 50, thereby tightly filling an associated space. By means of the talc ring 26 and the talc ring 22, previously placed in the metal cup 20, the metal cup 20 and the sensor element 10 are held in position in the metallic shell 50. Airtightness within the metallic shell 50 is maintained by means of the crimp packing 29 intervening between the crimp portion 53 and the shoulder portion 28 of the sleeve 27, thereby preventing outflow of combustion gas.

The rear end portion 12 of the sensor element 10 projects rearward beyond the rear end (crimp portion 53) of the metallic shell 50. The rear end portion 12 is covered with a tubular separator 60 formed from an insulating ceramic. The separator 60 internally holds the five electrode pads 16 formed on the rear end portion 12 of the sensor element 10 and five connection terminals 61 (one of which is shown in FIG. 1), which are electrically connected to the respective electrode pads 16. Also, the separator 60 protectively accommodates connections between the connection terminals 61 and corresponding five lead wires 65 (three of which are shown in FIG. 1), extending to the exterior of the gas sensor 1.

The tubular sheath 30 is disposed so as to circumferentially enclose the rear end portion 12 of the sensor element 10 to which the separator 60 is fitted. The sheath 30 is made of stainless steel (e.g., SUS304). A front open end 31 of the sheath 30 engages the outer circumference of the rear-end engaging-portion 57 of the metallic shell 50. The open end 31 is crimped radially inward, and laser welding is performed on the open end 31 along the outer circumference thereof, whereby the open end 31 is joined to the rear-end engaging-portion 57. The sheath 30 and the metallic shell 50 are thus united.

A tubular metal holder 70 is disposed in the clearance between the sheath 30 and the separator 60. The metal holder 70 has a support portion 71, which is formed by inwardly bending a rear end of the metal holder 70. The separator 60 is inserted through the metal holder 70 such that a flange portion 62 formed on the outer circumference of a rear end portion of the separator 60 engages the support portion 71, whereby the separator 60 is supported by the support portion 71. In this condition, a portion of the sheath 30 where the metal holder 70 is disposed is crimped radially inward, whereby the metal holder 70 which supports the separator 60 is fixed to the sheath 30.

A grommet 75 made of fluorine-containing rubber is fitted into a rear end opening of the sheath 30. The grommet 75 has five insertion holes 76 (one of which is shown in FIG. 1). The five lead wires 65 extending outwardly from the separator 60 are airtightly inserted through the respective insertion holes 76. In this condition, a portion of the sheath 30 which corresponds to the grommet 75 is crimped radially inward, whereby the grommet 75 is fixed to the rear end of the sheath 30 while pressing the separator 60 frontward.

While the sensor element 10 is held in the metallic shell 50, the detecting portion 11 of the sensor element 10 projects from a front end portion (front-end engaging-portion 56) of the metallic shell 50. The protector 100 is fitted to and laser-welded to the front-end engaging-portion 56 for the purpose of protecting the detecting portion 11 of the sensor element 10 from contamination with deposits (poisonous adhering substances such as fuel ash and oil component) contained in exhaust gas and from adhering water droplets which would result in breakage or the like of the detecting portion 11. The protector 100 has a dual-structure consisting of a closed-bottomed tubular inner protector 120 having a plurality of holes formed in its side wall, and an outer protector 110, which assumes a tubular form so as to circumferentially enclose the inner protector 120 with a clearance (a gas separation chamber 119 (see FIG. 2)) formed between an outer circumferential surface of the inner protector 120 and an inner circumferential surface of the outer protector 110 and which has a plurality of holes formed in its side wall.

As shown in FIG. 2, the inside diameter of the inner protector 120 is smaller than the outside diameter of the front-end engaging-portion 56 of the metallic shell 50. A rear end portion 121 associated with an open end (rear end) of the inner protector 120 is expanded in diameter so as to engage the front-end engaging-portion 56. A side wall 122 of the inner protector 120 has a plurality of (six in the present embodiment) inner introduction holes 130 which are arranged circumferentially at a position X located toward the rear end portion 121 with respect to the direction of the axis O. The side wall 122 also has a plurality of (six in the present embodiment) inner introduction holes 140 which are arranged circumferentially and located at a position Y located frontward of the position X with respect to the direction of the axis O. The inner introduction holes 130 and 140 are adapted to introduce mainly a gas component of exhaust gas, which is introduced into the clearance (the gas separation chamber 119) formed between the outer protector 110 and the inner protector 120 through outer introduction holes 115 of the outer protector 110 described below, into the interior of the inner protector 120; i.e., into a detection chamber 129 to which the detecting portion 11 of the sensor element 10 is exposed. The inner introduction holes 130 and 140 are located rearward of the front end of the sensor element 10. The relative arrangement of the inner introduction holes 130 and 140 will be described in detail below. The position X with respect to the direction of the axis O corresponds to the "second position" in the present invention, and the inner introduction holes 130 correspond to the "second inner introduction holes" in the present invention. The position Y with respect to the direction of the axis O corresponds to the "first position" in the present invention, and the inner introduction holes 140 correspond to the "first inner introduction holes" in the present invention.

A front end portion of the side wall 122 of the inner protector 120 has drain holes 150 which wedgewise open into the interior of the inner protector 120 and which are arranged at a plurality of (three in the present embodiment) circumferential positions. The drain holes 150 are located frontward of the front end of the sensor element 10. A bottom wall 123 of the inner protector 120 has a drainage port 160.

Next, as in the case of the inner protector 120, a rear end portion 111 of the outer protector 110 associated with an open end of the outer protector 110 has an expanded diameter. The rear end portion 111 is engaged with the rear end portion 121 of the inner protector 120. Laser welding is performed along the entire circumference of the rear end portion 111 of the outer protector 110 so as to fix the rear end portion 111 of the outer protector 110 and the rear end portion 121 of the inner protector 120 to the front-end engaging-portion 56. An end portion 113 located at the front end of the outer protector 110 is bent inward, at a position in the vicinity of the bottom wall 123 of the inner protector 120, toward the outer circumferential surface of the inner protector 120. This closes the clearance formed between the outer circumferential surface of the inner protector 120 and the inner circumferential surface of the outer protector 110 at the front end of the clearance, thereby forming the gas separation chamber 119.

A front end portion of a side wall 112 of the outer protector 110 has a plurality of (eight in the present embodiment) outer introduction holes 115 which are arranged circumferentially at a position located frontward of the above-mentioned position Y with respect to the direction of the axis O and which are adapted to establish atmospheric communication between the exterior and the interior of the outer protector 110. Each of the outer introduction holes 115 has a guide portion 116 which extends inward. The guide portions 116 cause exhaust gas, which is externally introduced into the gas separation chamber 119 through the outer introduction holes 115, to swirl around the outer circumferential surface of the side wall 122 of the inner protector 120.

In the thus-configured gas sensor 1, in order to protect the detecting portion 11 of the sensor element 10 exposed to the detection chamber 129 (the interior of the inner protector 120) from the adverse effects of adhering water droplets, limitations are imposed on the size of the plurality of the inner introduction holes 130 and 140 formed in the inner protector 120. Specifically, in order to make a mass of water (water droplet) that has separated from a gas component within the gas separation chamber 119 unlikely to enter the detection chamber 129, the minimum opening length C of each of the inner introduction holes 130 and 140 (in the present embodiment, since each of the inner introduction holes 130 and 140 is circular, the diameter of the hole is a minimum opening length) is set to 1.5 mm. By limiting the minimum opening length C of each of the inner introduction holes 130 and 140 to 2 mm or less, a spherical water droplet having a diameter greater than 2 mm does not pass through the inner introduction holes 130 and 140. This more effectively restricts the amount and size of water droplets which could adhere to the detecting portion 11 of the sensor element 10 accommodated within the inner protector 120, so that cracking, breakage, or the like can be prevented. A smaller minimum opening length C of the individual inner introduction holes 130 and 140 more reliably restricts entry of water droplets into the detecting chamber 129. Consequently, laser machining, plasma arc machining, or a like method must be employed for industrially forming holes having such a small size. This kind of machining involves troublesome work and raises production cost. In order to improve production efficiency, the use of a punch or a like jig is preferred. In view of durability of such a jig, a minimum opening length C of each of the inner introduction holes 130 and 140 of 1.5 mm or more is desirable.

The inner introduction holes 130 and 140 individually have an opening area of 1.77 mm² (i.e., an opening area of 3.5 mm² or less), thereby preventing entry of a water droplet having a diameter greater than the size of the opening of the respective inner introduction holes 130 and 140 into the interior of the inner protector 120 through the inner introduction holes 130 and 140. This restricts the amount and size of water droplets which could adhere to the detecting portion 11 of the sensor element 10 accommodated within the inner protector 120. Therefore, the amount of adhering water droplets, if any, can be very small, so that energy of thermal shock imparted to the sensor element 10 becomes small, thereby preventing the occurrence of cracking, breakage, or the like. Meanwhile, limiting the opening area as mentioned above may possibly deteriorate replaceability (i.e., increase residence time) of gas in the gas detection chamber 129 because of a reduction in the opening area of the individual inner introduction holes 130 and 140. In order to cope with this problem, on the basis of the results of an evaluation test of Example 1, described below, the present invention prescribes a total opening area of the inner introduction holes 130 and 140 of 10 mm² or more. By way of example, the present embodiment employs six inner introduction holes 130 each having an opening area of 1.77 mm² and six inner introduction holes 140 each having an opening area of 1.77 mm². Thus, the total opening area becomes 21.2 mm², so that sufficient gas replaceability can be ensured. By employing a total opening area of all the inner introduction holes 130 and 140 of 10 mm² or more, the entire inner protector 120 has a sufficiently large opening area of the inner introduction holes 130 and 140. Therefore, gas replaceability does not suffer, so that the sensor element 10 can exhibit sufficiently high gas response.

Furthermore, since the inner introduction holes 130 and 140 are formed in a total number of six or more, while the total opening area of the inner introduction holes 130 and 140 is maintained at 10 mm² or more, the opening area of the individual inner introduction holes 130 and 140 can be reduced further. Thus, cracking, breakage, etc., of the sensor element 10 accommodated within the inner protector 120 can be prevented more effectively.

The drain holes 150 are adapted to introduce water droplets trapped in the clearance between the outer protector 110 and the inner protector 120 into the interior of the inner protector 120 for the purpose of draining the water droplets from the drainage port 160. In view of efficiency in drainage of water droplets, the drain holes 150 are located frontward of the outer introduction holes 115. In order to prevent water droplets present in exhaust from adhering to the sensor element 10, which enter through the drain holes 150, the drain holes 150 are located frontward of the sensor element 10 and do not correspond to the "inner introduction holes" defined herein.

Figure 3:
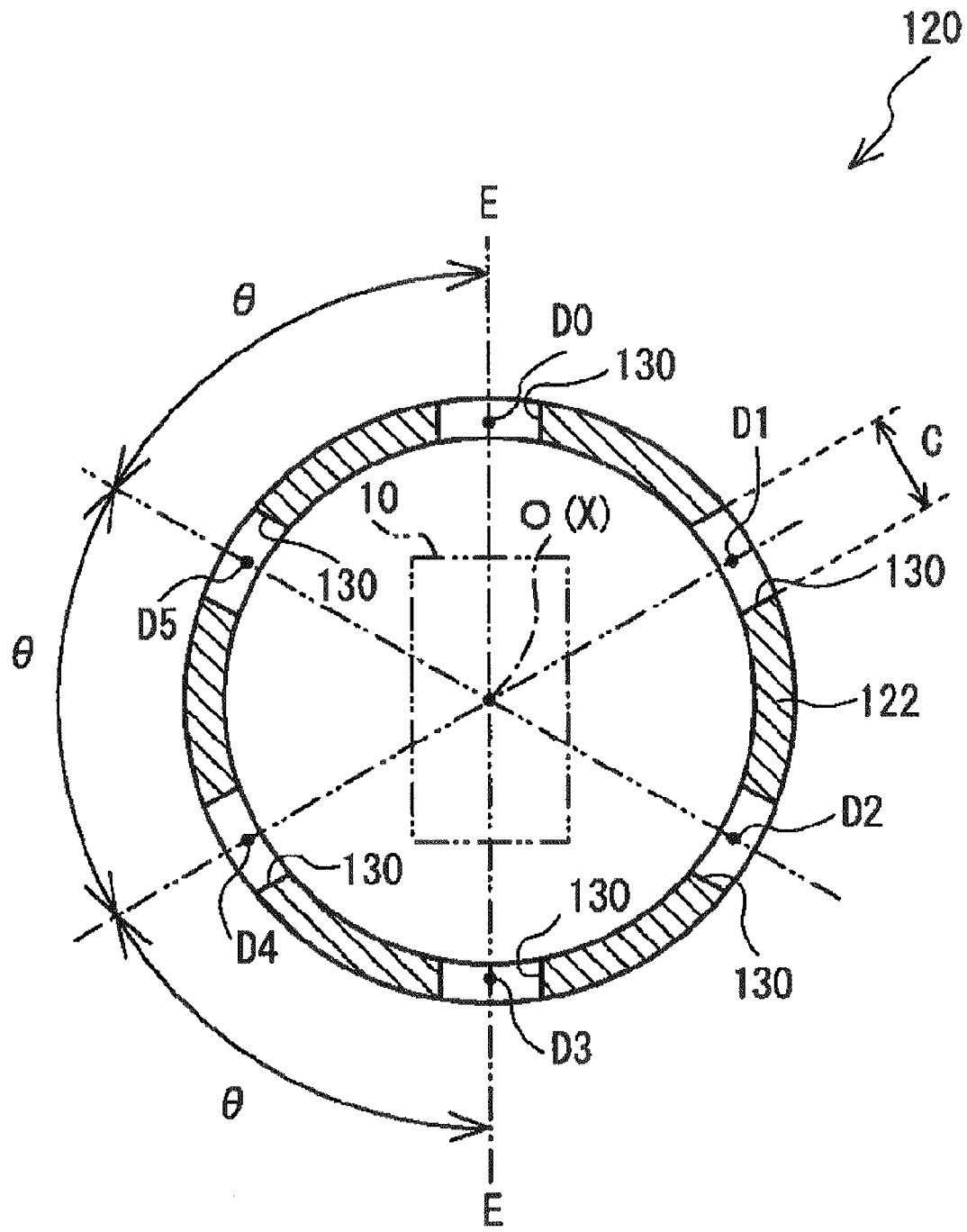
FIG. 3 is a sectional view of an inner protector 120 taken along the dash-dot-dot line A-A of FIG. 2.
Figure 4:
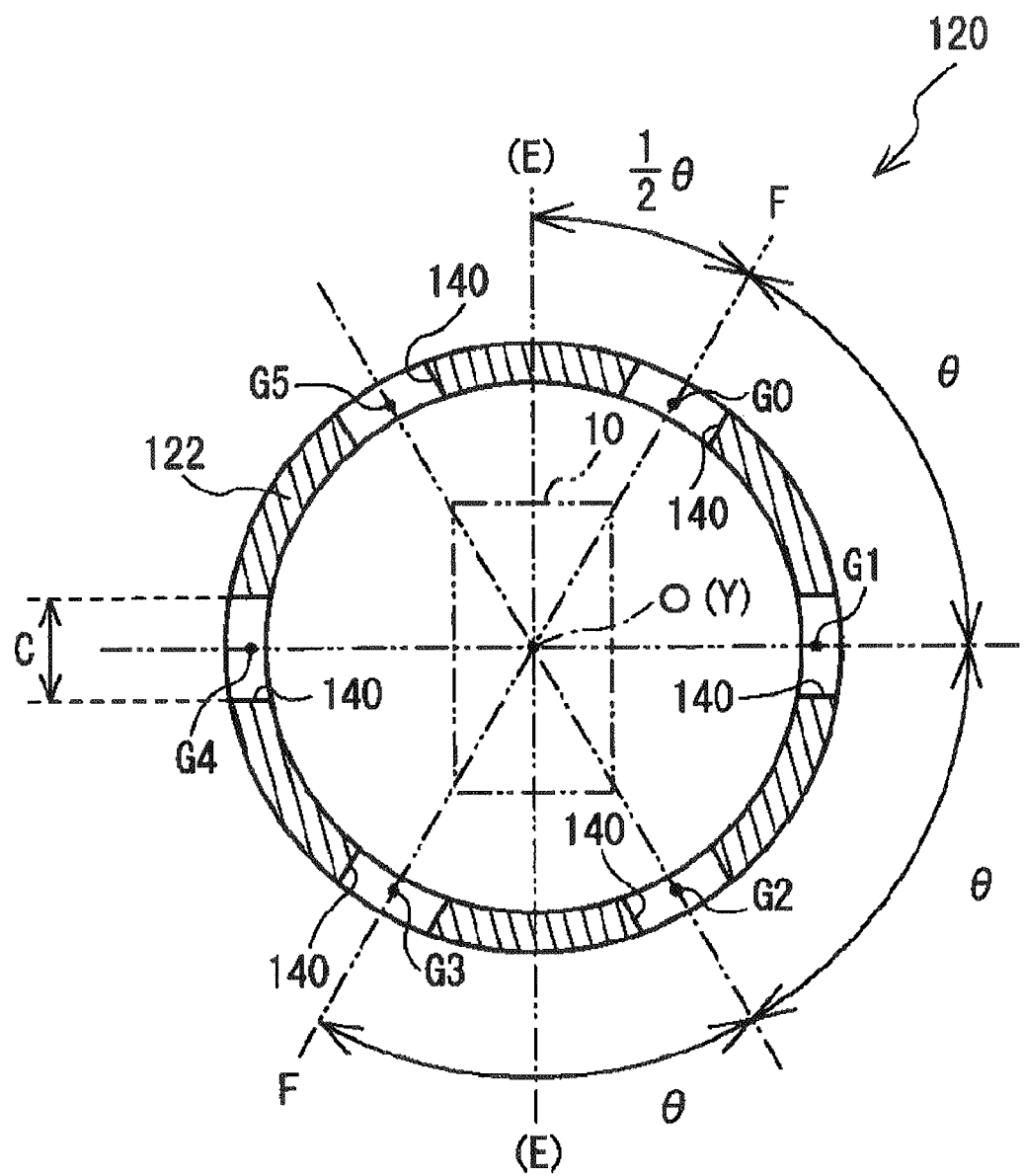
FIG. 4 is a sectional view of the inner protector 120 taken along the dash-dot-dot line B-B of FIG. 2.
Figure 5:
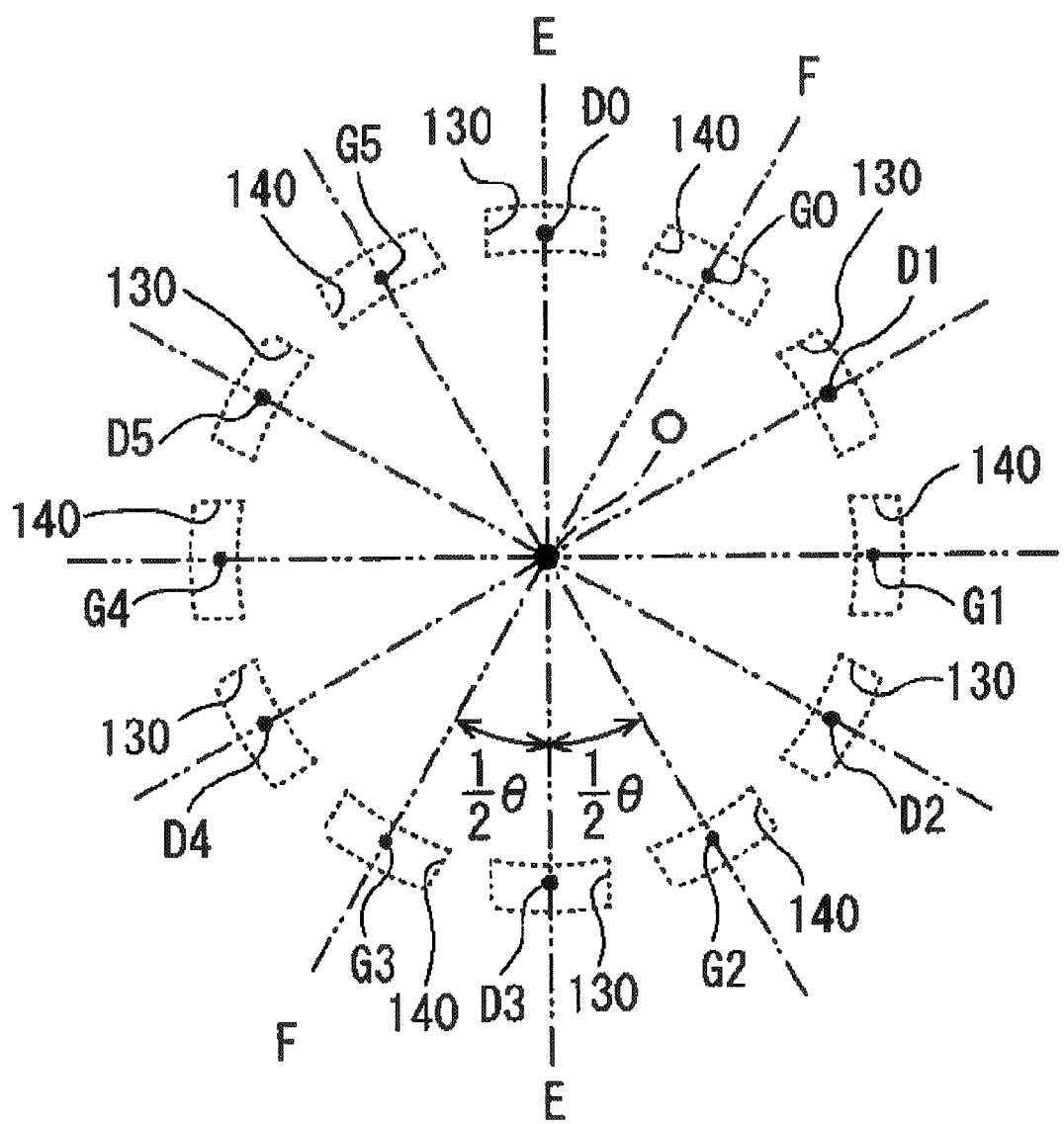
FIG. 5 is a view of inner introduction holes 130 and inner introduction holes 140 superposed on an imaginary plane which orthogonally intersects with an axis O.

In order to prevent loss of strength of the inner protector 120, limitations are imposed on the number and the relative arrangement of the inner introduction holes 130 and 140. These limitations will next be described with reference to FIGS. 2 to 5. FIG. 3 is a sectional view of the inner protector 120 taken along the dash-dot-dot line A-A of FIG. 2. FIG. 4 is a sectional view of the inner protector 120 taken along the dash-dot-dot line B-B of FIG. 2. FIG. 5 is a view of the inner introduction holes 130 and the inner introduction holes 140 which are superposed on an imaginary plane which intersects orthogonally with the axis O.

As mentioned previously, the side wall 122 of the inner protector 120 shown in FIG. 2 has a plurality of the inner introduction holes 130 and 140. A plurality of (six in the present embodiment) of the inner introduction holes 130 are formed in the side wall 122 while being arranged circumferentially at the position X located toward the rear end portion 121 with respect to the direction of the axis O. A plurality of (six in the present embodiment) the inner introduction holes 140 are formed in the side wall 122 while being arranged circumferentially at the position Y located frontward of the position X with respect to the direction of the axis O.

As shown in FIG. 3, on an imaginary plane (corresponding to paper plane of FIG. 3) which includes the position X on the axis O and intersects orthogonally with the axis O, a position D0 is one of two intersections of an imaginary straight line E-E passing through the position of the axis O, and the side wall 122 of the inner protector 120. With the position Do serving as a reference position, positions D1, D2, . . . , and D5 are arranged on the side wall 122 at equal angular intervals θ degrees (e.g., 60 degrees) about the position of the axis O. The inner introduction holes 130 have their centers at the positions D0, D1, . . . , D5, respectively; extend through the side wall 122 of the inner protector 120 across the thickness of the side wall 122; and have an inside diameter C (e.g., 1.5 mm).

As shown in FIG. 4, on an imaginary plane (corresponding to the paper plane of FIG. 4) which includes the position Y on the axis O and intersects orthogonally with the axis O and on which the above-mentioned imaginary straight line E-E is superposed, turning the imaginary straight line E-E about the position of the axis O by an angle (θ/2 degrees in the present embodiment) greater than 0 degree and smaller than θ degrees makes the straight line E-E coincide with an imaginary straight line F-F. A position G0 is one of two intersections of the imaginary straight line F-F and the side wall 122 of the inner protector 120. Similarly to the above-described arrangement, with the position G0 serving as a reference position, positions G1, G2, . . . , and G5 are arranged on the side wall 122 at equal angular intervals θ degrees (e.g., 60 degrees) about the position of the axis O. As in the case of the inner introduction holes 130, the inner introduction holes 140 have their centers at the positions G0, G1, . . . , G5, respectively; extend through the side wall 122 of the inner protector 120 across the thickness of the side wall 122; and have an inside diameter C (e.g., 1.5 mm).

As shown in FIG. 5, when the inner introduction holes 130 and the inner introduction holes 140 are superposed on an imaginary plane (corresponding to the paper plane of FIG. 5) which intersects orthogonally with the same axis O, the inner introduction holes 130 whose centers coincide with the positions D0, D1, . . . , D5, respectively, and the inner introduction holes 140 whose centers coincide with the positions G0, G1, . . . , G5, respectively, are arranged alternately in a circumferential direction about the position of the axis O at angular intervals of θ/2 degrees. Thus, on the outer circumferential surface of the side wall 122 of the inner protector 120 shown in FIG. 2, the center positions of the inner introduction holes 130 and the center positions of the inner introduction holes 140 do not coincide with one another with respect to the direction of the axis O.

Preferably, the relative arrangement of the inner introduction holes 130 and the inner introduction holes 140 is determined such that, when the center positions of the inner introduction holes 130 and the center positions of the inner introduction holes 140 are superposed on the imaginary plane which intersects orthogonally with the axis O as shown in FIG. 5, the distance between the adjacent center positions of the inner introduction holes 130 and 140 is greater than the distance C (inside diameter of the inner introduction holes 130 and 140) in the circumferential direction with respect to the axis O. In other words, desirably, the inner introduction holes 130 and the inner introduction holes 140 are arranged so as not to overlap one another with respect to the direction of the axis O of the side wall 122. This arrangement can reduce variations in distance between a certain inner introduction hole 130 and a certain inner introduction hole 140, whereby the strength of the inner protector 120 can be maintained. More preferably, when the inner introduction holes 130 and 140 are superposed on the imaginary plane of FIG. 5 which intersects orthogonally with the axis O, the center positions of the inner introduction holes 130 and 140 are arranged at equal intervals in a circumferential direction. This arrangement can eliminate variations in distance between a certain inner introduction hole 130 and a certain inner introduction hole 140, whereby the strength of the inner protector 120 can be maintained more reliably.

According to the present embodiment, the side wall 122 of the inner protector 120 has six inner introduction holes 130 and six inner introduction holes 140 which are arranged at equal intervals in a circumferential direction. When the gas sensor 1 is attached to an exhaust pipe of an automobile (not shown), the flow direction of exhaust gas is perpendicular or substantially perpendicular to the direction of the axis O. Since the three or more inner introduction holes 130 and the three or more inner introduction holes 140 are arranged at equal intervals in a circumferential direction, after attaching the gas sensor 1 to the exhaust pipe, even if any circumferential portion of the outer circumferential surface of the inner protector 120 faces upstream with respect to the flow direction of exhaust gas, any one of the inner introduction holes 130 and 140 can face upstream with respect to the flow direction of exhaust gas. Similarly, the outer introduction holes 115 of the outer protector 110 are arranged at equal intervals in a circumferential direction.

According to the present embodiment, the gas introduction portion 17 of the sensor element 10 is disposed between the inner introduction holes 130 and the inner introduction holes 140 with respect to the axial direction. This shortens the distance between the inner introduction holes 130 and the gas introduction portion 17 and the distance between the inner introduction holes 140 and the gas introduction portion 17, whereby exhaust gas can be promptly introduced to the detecting portion 11. Thus, the gas response of the sensor element 10 can be enhanced.

Next, a second embodiment of the present invention will be described with reference to FIG. 6. A gas sensor 500 of the second embodiment differs from the gas sensor 1 of the above-described first embodiment only in the shape of the inner protector and has other structural features substantially similar to those of the gas sensor 1. Therefore, the following description centers on an inner protector 620.

As in the case of the above-described first embodiment, in the gas sensor 500 of the second embodiment, the protector 600 is fitted to and laser-welded to a metallic shell 550 for the purpose of protecting a detecting portion 511 of a sensor element 510 from breakage or the like which could otherwise result from contamination with deposits (poisonous adhering substances such as fuel ash and oil component) contained in exhaust gas and adhering water droplets. The protector 600 has a dual-structure consisting of a closed-bottomed tubular inner protector 620 having a plurality of holes formed in its side wall, and an outer protector 610, which assumes a tubular form so as to circumferentially enclose the inner protector 620 with a clearance (a gas separation chamber 619 (see FIG. 6)) formed between an outer circumferential surface of the inner protector 620 and an inner circumferential surface of the outer protector 610 and which has a plurality of holes formed in its side wall.

A rear end portion 611 of the outer protector 610 associated with an open end of the outer protector 610 has an expanded diameter. The rear end portion 611 engages a rear end portion 621 of the inner protector 620, which will be described below. Laser welding is performed along the entire circumference of the rear end portion 611 of the outer protector 610 so as to fix the rear end portion 611 of the outer protector 610 and the rear end portion 621 of the inner protector 620 to the metallic shell 550. An end portion 613 located at the front end of the outer protector 610 is bent inward, at a position in the vicinity of a bottom wall 623 of the inner protector 620 to be described below, toward the outer circumferential surface of the inner protector 620. This closes a clearance formed between the outer circumferential surface of the inner protector 620 and the inner circumferential surface of the outer protector 610 at the front end of the clearance, thereby forming the gas separation chamber 619.

A front end portion of a side wall 612 of the outer protector 610 has a plurality of (eight in the present embodiment) outer introduction holes 615 which are arranged circumferentially at a position located frontward of the sensor element 510 to be described below and which are adapted to establish atmospheric communication between the exterior and the interior of the outer protector 610. Each of the outer introduction holes 615 has a guide portion 616 which extends inward. The guide portions 616 cause exhaust gas, which is externally introduced into the gas separation chamber 619 through the outer introduction holes 615, to swirl around the outer circumferential surface of a side wall 622 of the inner protector 620, which will be described below.

Figure 6:
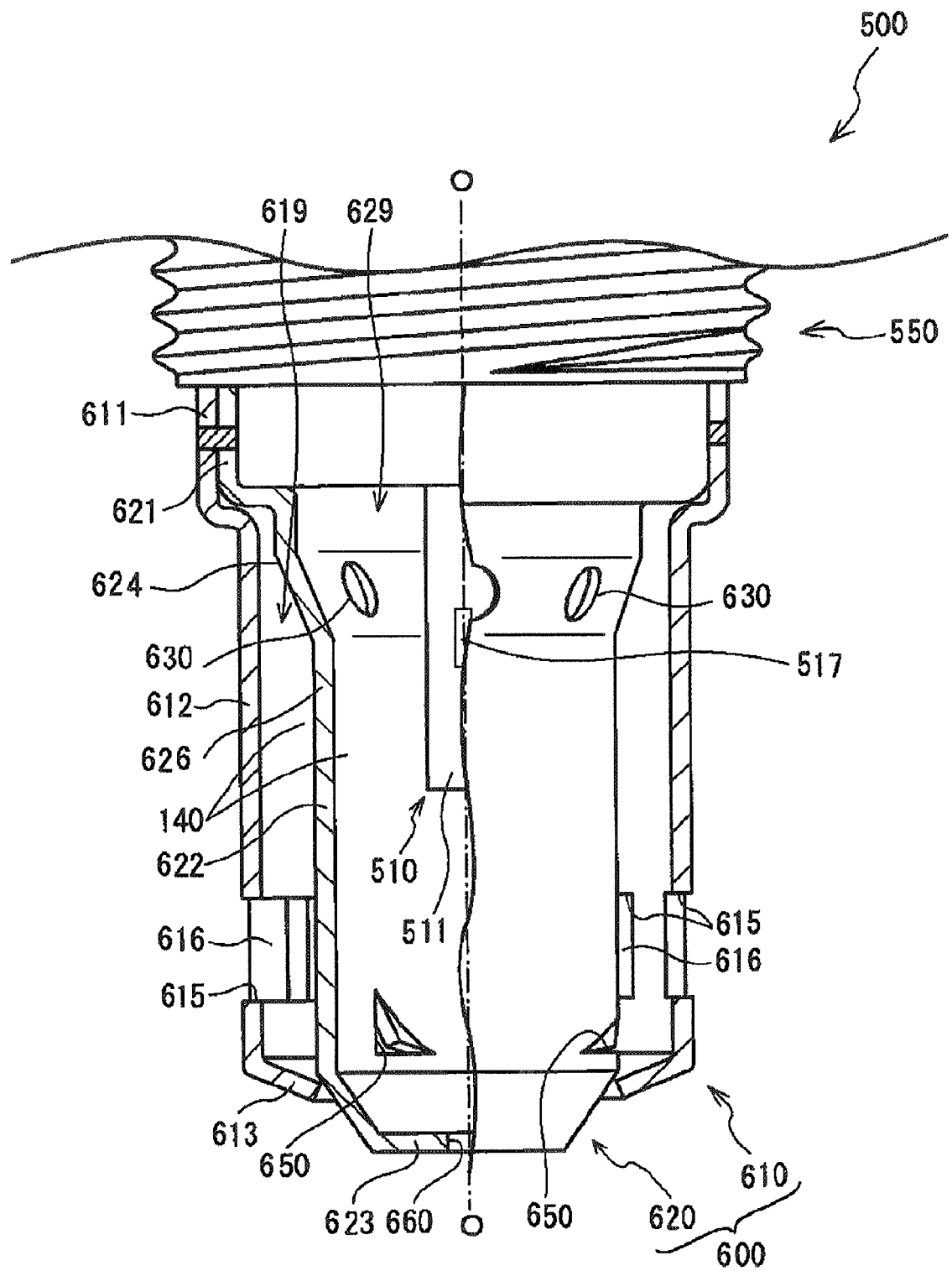
FIG. 6 is a partial sectional view on an enlarged scale of a front end portion of a gas sensor 500 according to a second embodiment.

As shown in FIG. 6, a rear end portion 621 associated with an open end (rear end) of the inner protector 620 has an expanded diameter so as to engage the metallic shell 550. The side wall 622 of the inner protector 620 has a taper portion 624 whose diameter radially reduces toward the front-end side. The taper portion 624 has a plurality of (eight in the present embodiment) inner introduction holes 630 which are arranged circumferentially. The inner introduction holes 630 are adapted to introduce mainly a gas component of exhaust gas, which is introduced into the clearance (the gas separation chamber 619) formed between the outer protector 610 and the inner protector 620 through the outer introduction holes 615 of the outer protector 610, into the interior of the inner protector 620; i.e., into a detection chamber 629 to which the detecting portion 511 of the sensor element 510 is exposed. The inner introduction holes 630 are located rearward of the front end of the sensor element 510.

A front end portion of the side wall 622 of the inner protector 620 has drain holes 650 which wedgewise open into the interior of the inner protector 620 and which are arranged at a plurality of (three in the present embodiment) circumferential positions. The drain holes 650 are located frontward of the front end of the sensor element 10. A bottom wall 623 of the inner protector 620 has a drainage port 660.

In the case where the inner protector 620 has the taper portion 624 as mentioned above, by means of the inner introduction holes 630 formed in the taper portion 624, even when a water droplet smaller than the inner introduction hole 630 enters the interior of the inner protector 620, the water droplet adheres to a portion of the sensor element 510 which is located rearward of the detecting portion 511 of the sensor element 510 and which is relatively low in temperature. Thus, the detecting portion 511 of the sensor element 510 becomes unlikely to be subjected to thermal shock, so that cracking, breakage, or the like can be prevented.

Furthermore, in the second embodiment, the gas introduction portion 517 of the sensor element 510 is disposed such that the gas introduction portion 517 faces, in a crossing manner, the boundary between the taper portion 624 and a tubular portion 626 continuous with the front end of the taper portion 624. By virtue of such arrangement, the distance between the inner introduction holes 630 and the gas introduction portion 617 is shortened, whereby exhaust gas can be promptly introduced to the detecting portion 611. As a result, while the occurrence of cracking, breakage, or the like of the sensor element 510 is effectively prevented, the gas response of the sensor element 510 can be more effectively enhanced.

EXAMPLE 1

In order to verify the effect of imposing limitations on the size, number, and relative arrangement of the inner introduction holes 130 and 140, first, an evaluation test was carried out with respect to the relationship between the total opening area of the inner introduction holes 130 and 140 formed in the inner protector 120 and gas replaceability.

In this evaluation test, the following were prepared: a first sample of an inner protector having three inner introduction holes arranged at equal intervals in a circumferential direction at the same position with respect to the direction of the axis O; a second sample of an inner protector having six inner introduction holes arranged at equal intervals in a circumferential direction at the same position with respect to the direction of the axis O; and a third sample of an inner protector equivalent to the inner protector 120 of the present embodiment having six inner introduction holes arranged at equal intervals in a circumferential direction at each of two different positions with respect to the direction of the axis O, so that a total of 12 inner introduction holes were provided. In the first to third samples, each of the inner introduction holes had an opening area of 1.77 mm$^2$ (a circular hole having a diameter of 1.5 mm). Also, as a comparative example, a fourth sample of an inner protector was prepared having six conventional inner introduction holes of oblong shape in the direction of the axis O and arranged at equal intervals in a circumferential direction at the same position with respect to the direction of the axis O. The total opening area of the inner introduction holes of the first sample was 5.3 mm$^2$, and the total opening area of the inner introduction holes of the second sample was 10.6 mm$^2$. The total opening area of the inner introduction holes of the third sample was 21.2 mm$^2$, and the total opening area of the inner introduction holes of the fourth sample was 36.8 mm$^2$.

Gas sensors of each of the first to fourth samples were fabricated. Using propane gas, a desk test for gas response was carried out on the gas sensors. Specifically, the gas sensors were placed in an atmosphere in which propane gas was burned using a burner in a controlled manner such that a $\lambda$ value indicative of an excess air ratio to propane gas alternated between 0.9 and 1.1 at a constant frequency (e.g., every second). By means of measuring the difference between the timing of alternation of the $\lambda$ value when propane gas was supplied to the burner, and the timing of alternation of the $\lambda$ value which each of the gas sensors detected, a response time which elapsed until 63% of an output of the gas sensor was reached was measured. The gas sensors differed from one another only in the structure of the inner protector. Thus, the level of gas response indicates the level of gas replaceability between the interior and the exterior of the inner protector.

Figure 7:
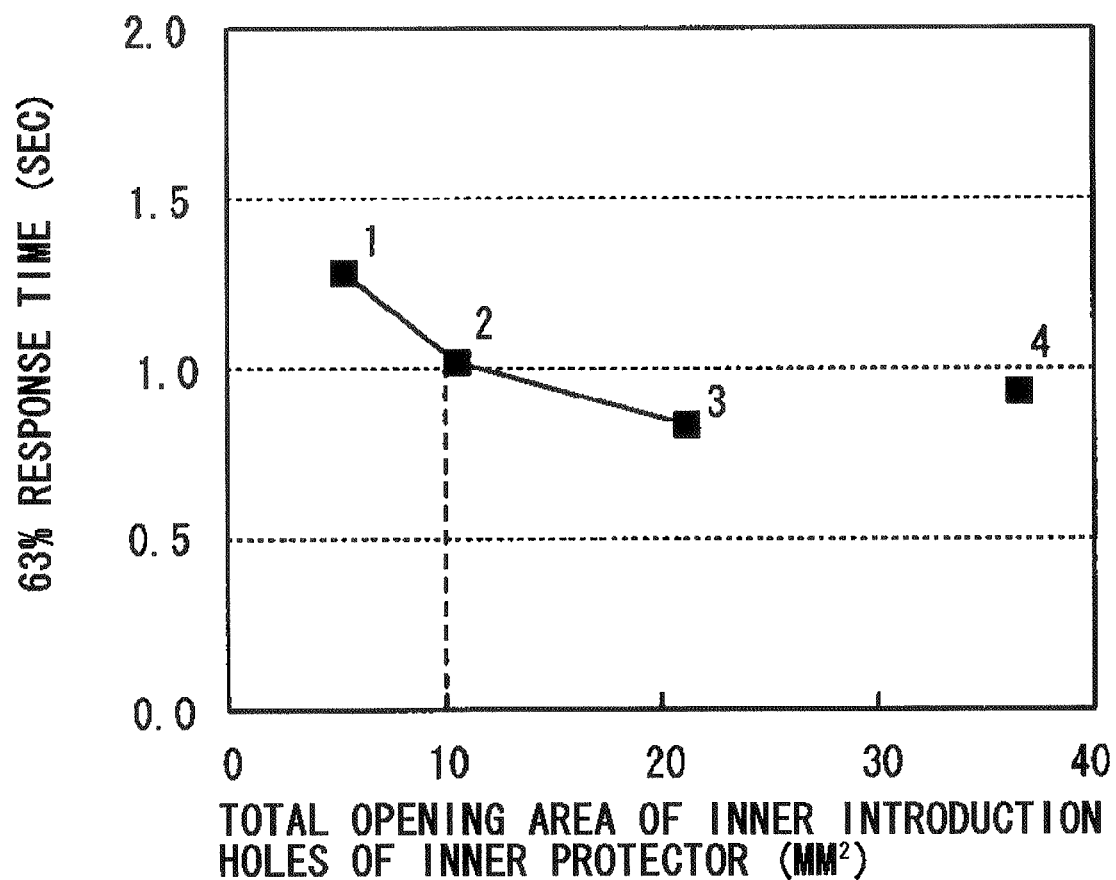
FIG. 7 is a graph showing the relationship between the total opening area of inner introduction holes and gas sensor response.

The gas sensor of the first sample exhibited a response time of about 1.3 sec. The gas sensors of the second and third samples exhibited a response time of about 1.0 sec and about 0.8 sec, respectively. The gas sensor of the fourth sample, which is a comparative example, exhibited a response time of about 0.95 sec. The graph of FIG. 7 shows the results of the evaluation test. In the graph of FIG. 7, numbers assigned to respective points indicate sample numbers.

As is apparent from the graph of FIG. 7, as the number of inner introduction holes increases; i.e., as the total opening area of the inner introduction holes increases, the response time of the gas sensor shortens, indicating that the response time (gas replaceability of the inner protector) of the gas sensor quickens. There was little difference in response time between the gas sensor of the second sample and the gas sensor of the fourth sample. Furthermore, the gas sensor of the third sample had a shorter response time than the gas sensor of the fourth sample. Although the third sample had a total opening area of the inner introduction holes smaller than that of the fourth sample, the third sample exhibited better gas response than the fourth sample. These results reveal that a gas sensor employing an inner protector having at least six holes exhibits quick gas response; i.e., gas replaceability of the inner protector equivalent to or higher than that of a conventional gas sensor.

EXAMPLE 2

Next, an evaluation test was carried out to assess the relationship between the opening area of each of the inner introduction holes 130 and 140 of the inner protector 120 and protection of the sensor element 10 from adhering water droplets. In this evaluation test, three samples were prepared, namely, eighth, ninth and tenth samples, each equivalent to the inner protector 120 of the present embodiment having six inner introduction holes arranged at equal intervals in a circumferential direction at each of two different positions with respect to the direction of the axis O, so as to provide a total of 12 inner introduction holes 130 and 140. Each of the inner introduction holes 130 and 140 of the eighth to tenth samples had an opening area of 1.77 mm$^2$ (a circular hole having a diameter of 1.5 mm). Similarly, eleventh, twelfth and thirteenth samples were prepared which were variants of the eighth to tenth samples and in which each of the inner introduction holes 130 and 140 had an opening area of 3.14 mm$^2$ (a circular hole having a diameter of 2.0 mm). Also, as comparative examples, three samples were prepared, namely, fifth, sixth and seventh samples, each having six conventional inner introduction holes of oblong shape in the direction of the axis O and arranged at equal intervals in a circumferential direction at the same position with respect to the direction of the axis O. Each of the inner introduction holes of the fifth to seventh samples had an opening area of 6.1 mm$^2$ and an opening width allowing passage of a sphere having a maximum diameter of 2.0 mm.

Figure 8:
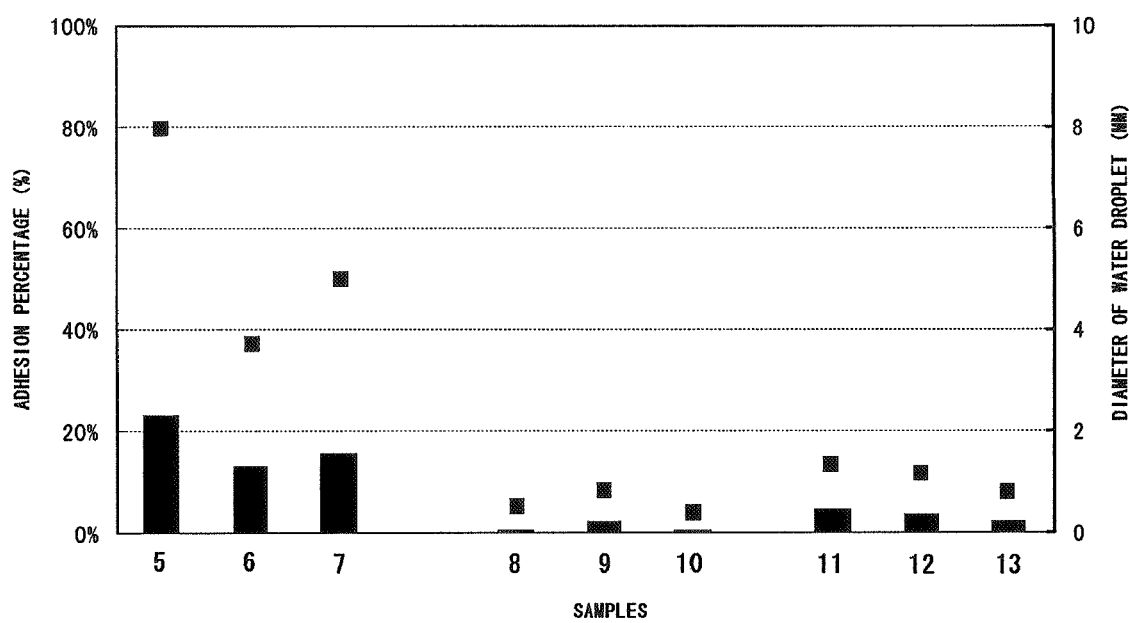
FIG. 8 is a graph showing the relationship between the opening area of a single inner introduction hole and protection of a gas sensor from adhering water droplets.

Gas sensors 1 which respectively had the fifth to thirteenth samples were fabricated. In this assembly work, carbon was applied to the surface of the sensor element 10 of each of the gas sensors 1. Next, the gas sensors 1 were set in an evaluation test apparatus and subjected to a test operation for 30 seconds. Subsequently, the gas sensors 1 were unloaded from the evaluation test device, and the samples were removed from the gas sensors 1. Then, the condition of the sensor elements 10 was examined. When a water droplet adheres to the surface of the sensor element 10, a corresponding piece of carbon exfoliates, thereby leaving a snow flake at a position of adhesion of the water droplet. The sensor elements 10 of the samples were visually examined for an approximate percentage of snow flake area to the entire carbon-applied area (adhesion percentage of water droplets). Also, the diameter of a snow flake associated with adhesion of a water droplet having a maximum diameter; i.e., the maximum diameter of a water droplet having passed through the inner introduction hole 130 or 140, was measured. The test results are shown in FIG. 8. In FIG. 8, the bar graph represents the adhesion percentage of water droplets, and points represent the maximum diameter of a water droplet.

In the gas sensors of the eighth, ninth and tenth samples (an inner introduction hole has an opening area of 1.77 mm$^2$), the adhesion percentage of water droplets having passed through the inner introduction holes 130 and 140 was 2% or less, and the maximum diameter of a water droplet was 1 mm or less. In the gas sensors of the eleventh, twelfth and thirteenth samples (an inner introduction hole having an opening area of 3.14 mm$^2$), the adhesion percentage of water droplets having passed through the inner introduction holes 130 and 140 was 5% or less, and the maximum diameter of a water droplet was 1.5 mm or less. By contrast, in the gas sensors of the fifth, sixth and seventh samples (an inner introduction hole having an opening area of 6.1 mm$^2$), the adhesion percentage of water droplets having passed through the inner introduction holes 130 and 140, each having an opening width so as to allow passage of a sphere having a diameter of 2.0 mm, was 15% to 25%, and the maximum diameter of a water droplet was 8.0 mm.

The above test results demonstrate the following. As compared with the inner introduction holes formed in the inner protector of the conventional gas sensor, the inner introduction holes 130 and 140 each having an opening area of 3.5 mm$^2$ or less restrict the size of a water droplet capable of passing therethrough to a smaller size and further reduce the amount of water droplets passing therethrough, thereby effectively enhancing protection of the sensor element 10 from adhering water droplets.

The present invention is not limited to the above embodiments, and may be embodied in various other forms. For example, in the first embodiment, the inner introduction holes 130 and 140 are formed in the side wall 122 so as to be arranged circumferentially and located at different positions X and Y, respectively, with respect to the direction of the axis O; i.e., the inner introduction holes 130 and 140 are provided in two levels with respect to the direction of the axis O. However, the inner introduction holes may be provided at three or more positions; i.e., in three or more levels, with respect to the direction of the axis O.

Figure 9:
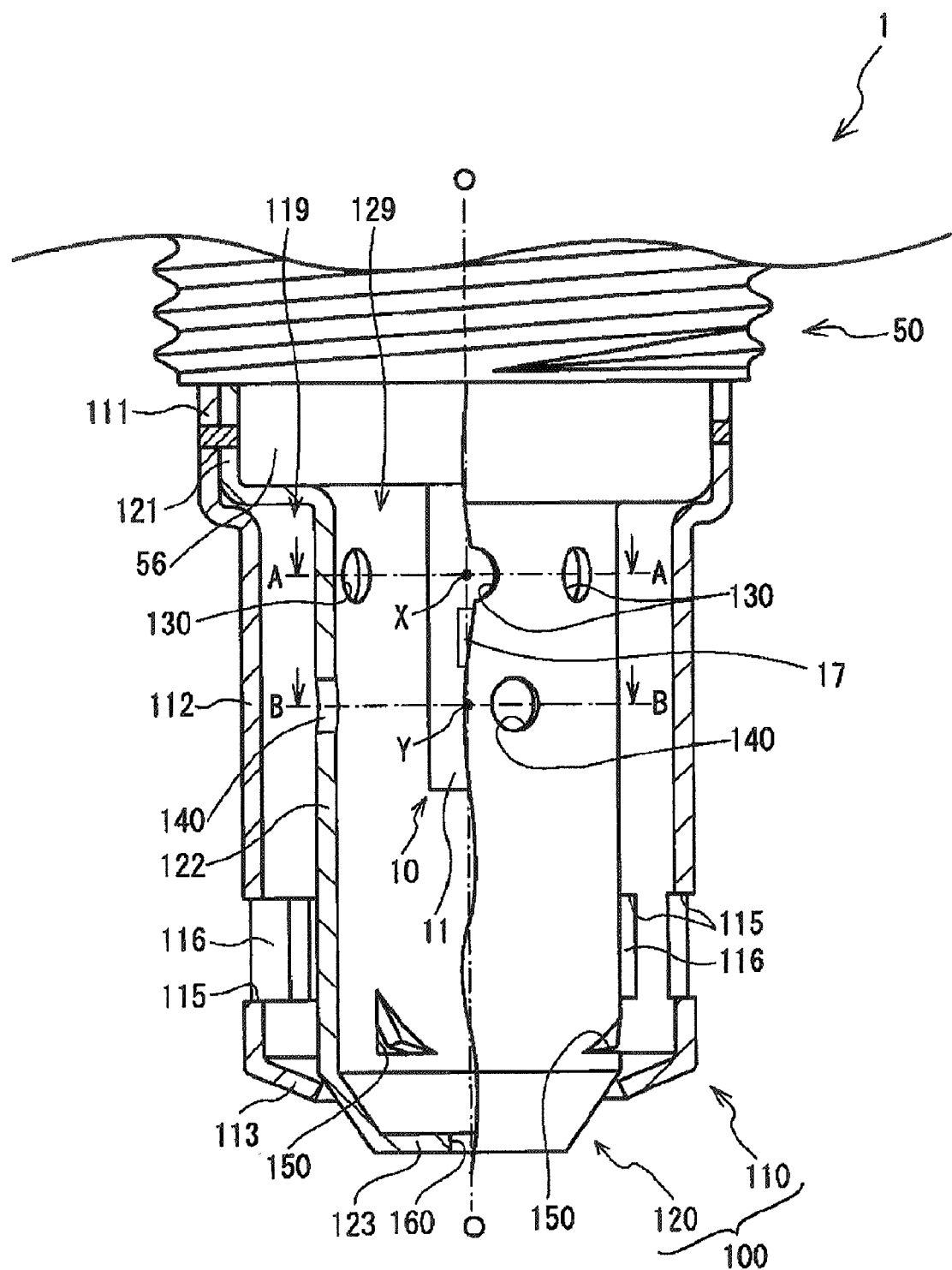
FIG. 9 is a partial sectional view on an enlarged scale of a front end portion of the gas sensor 1 according to a modified embodiment.

In the first embodiment, the inner introduction holes 130 and the inner introduction holes 140 are provided in the same number. However, the present invention is not limited thereto. As shown in FIG. 9, the number of the inner introduction holes 140 (three in FIG. 9) may be smaller than the number of the inner introduction holes 130 (six in FIG. 9). This enables exposure of the gas introduction portion 17 to a greater amount of exhaust gas introduced into the inner protector 120, whereby the gas response of the sensor element 10 can be more effectively enhanced.

The shape of the openings of the inner introduction holes 130 and 140 is not limited to a circle, so long as the opening area is 3.5 mm$^2$ or less. The inner introduction holes may be in the shape of an ellipse, polygon, or slit. In this case, preferably, the openings assume a shape so as not to allow passage of a sphere having a diameter greater than 2.0 mm. In view of durability of a jig used in manufacture, and the like, a circular shape is desirable.

In the first embodiment, even when the inner introduction holes 130 and the inner introduction holes 140 overlap one another with respect to the direction of the axis O, the strength of the inner protector 120 can be sufficiently maintained by means of increasing the distance between the position X and the position Y.

According to the present embodiment, the inner introduction holes 130 and 140 are formed in the side wall 122 so as to be desirably arranged at equal intervals in a circumferential direction. However, the inner introduction holes 130 and 140 are not necessarily arranged at equal intervals, so long as the strength of the inner protector 120 is sufficiently maintained. For example, the inner introduction holes 130 and 140 may be locally gathered around each of three points separated from one another at 120 degrees in a circumferential direction, with the points serving as centers for arranging the inner introduction holes 130 and 140. The above embodiments are described with application to a full-range air/fuel ratio sensor. However, the present invention is not limited thereto, and may be applied to protectors for use in oxygen sensors, NOx sensors, HC sensors, temperature sensors, etc.

Although the invention has been described above in relation to preferred embodiments and modifications thereof, it will be understood by those skilled in the art that other variations and modifications can be effected in these preferred embodiments without departing from the scope and spirit of the invention.

This application is based on Japanese Patent Application No. JP 2006-213476 filed Aug. 4, 2006 and Japanese Patent Application No. JP 2007-122528 filed May 7, 2007, the above-noted applications incorporated herein by reference in their entirety.

What is claimed is:

1. A gas sensor comprising:
a detecting element having a detecting portion provided at a front end portion of the detecting element and adapted to detect a specific gas component contained in a gas-to-be-measured;
a housing radially enclosing the detecting element, the detecting portion of the detecting element projecting from a front end of the housing;
an inner protector having a rear end portion fixed to a front end portion of the housing and accommodating the detecting portion, said inner protector having a plurality of inner introduction holes for introducing the gas-to-be-measured into the interior of the inner protector, the inner introduction holes being formed in a circumferential wall of the inner protector along a circumferential direction and located rearward of a front end of the detecting element; and
a cylindrical outer protector radially enclosing the inner protector such that a clearance is present between the inner protector and the outer protector, the outer protector having a rear end portion fixed to the front end portion of the housing and a plurality of outer introduction holes for introducing the gas-to-be-measured into the clearance, the outer introduction holes being formed in a circumferential wall of the outer protector along a circumferential direction and located frontward of the inner introduction holes of the inner protector with respect to an axial direction of the gas sensor,
wherein the inner introduction holes individually have an opening area of 3.5 mm$^2$ or less, and the total opening area of the inner introduction holes is 10 mm$^2$ or more,
wherein the circumferential wall of the inner protector has a taper portion whose diameter radially reduces toward a front end of the inner protector and the inner introduction holes are formed in the taper portion, and
wherein the inner protector has a tubular portion continuous with a front end of the taper portion, and the detecting element has a gas introduction portion for introducing the gas-to-be-measured into the interior of the detecting portion and the gas introduction portion is disposed such that the gas introduction portion faces, in a crossing manner, a boundary between the taper portion and the tubular portion.

2. The gas sensor according to claim 1, wherein the inner introduction holes individually have an opening area of 2 mm$^2$ or less.

3. The gas sensor according to claim 1, wherein the inner introduction holes individually have a minimum opening length of 2 mm or less.

4. The gas sensor according to claim 1, wherein the inner protector has six or more inner introduction holes.

5. The gas sensor according to claim 1, wherein the inner protector has eight or nine inner introduction holes.

6. The gas sensor according to claim 1, wherein the inner introduction holes are divided into a plurality of first inner introduction holes arranged circumferentially at a first position with respect to the axial direction and a plurality of second inner introduction holes arranged circumferentially at a second position located rearward of the first position with respect to an axial direction of the gas sensor.

7. The gas sensor according to claim 6, wherein the plurality of the first inner introduction holes and the plurality of the second inner introduction holes are arranged so as not to overlap one another in a circumferential direction.

8. The gas sensor according to claim 6, wherein the detecting element has a gas introduction portion for introducing the gas-to-be-measured into the interior of the detecting portion; and the gas introduction portion is disposed entirely between the first inner introduction holes and the second inner introduction holes with respect to the axial direction.

9. The gas sensor according to claim 7, wherein the detecting element has a gas introduction portion for introducing the gas-to-be-measured into the interior of the detecting portion; and the gas introduction portion is disposed between the first inner introduction holes and the second inner introduction holes with respect to the axial direction.

10. The gas sensor according to claim 8, wherein the number of the first inner introduction holes is smaller than the number of the second inner introduction holes.

11. The gas sensor according to claim 9, wherein the number of the first inner introduction holes is smaller than the number of the second inner introduction holes.

12. A gas sensor comprising:

a detecting element having a detecting portion provided at a front end portion of the detecting element and adapted to detect a specific gas component contained in a gas-to-be-measured;

a housing radially enclosing the detecting element, the detecting portion of the detecting element projecting from a front end of the housing;

an inner protector having a rear end portion fixed to a front end portion of the housing and accommodating the detecting portion, said inner protector having a plurality of inner introduction holes for introducing the gas-to-be-measured into the interior of the inner protector, the inner introduction holes being formed in a circumferential wall of the inner protector along a circumferential direction and located rearward of a front end of the detecting element; and a cylindrical outer protector radially enclosing the inner protector such that a clearance is present between the inner protector and the outer protector, the outer protector having a rear end portion fixed to the front end portion of the housing and a plurality of outer introduction holes for introducing the gas-to-be-measured into the clearance, the outer introduction holes being formed in a circumferential wall of the outer protector along a circumferential direction and located frontward of the inner introduction holes of the inner protector with respect to an axial direction of the gas sensor, wherein the inner introduction holes individually have an opening area of 3.5 mm$^2$ or less, and the total opening area of the inner introduction holes is 10 mm$^2$ or more, wherein the inner introduction holes are divided into a plurality of first inner introduction holes arranged circumferentially at a first position with respect to the axial direction and a plurality of second inner introduction holes arranged circumferentially at a second position located rearward of the first position with respect to an axial direction of the gas sensor, and wherein the detecting element has a gas introduction portion for introducing the gas-to-be-measured into the interior of the detecting portion and the gas introduction portion is disposed entirely between the first inner introduction holes and the second inner introduction holes with respect to the axial direction.

* * * * *